(12) United States Patent
Grote et al.

(10) Patent No.: US 9,296,699 B2
(45) Date of Patent: *Mar. 29, 2016

(54) REDUCTIVE AMINATION OF 6-KETO MORPHINANS BY CATALYTIC HYDROGEN TRANSFER

(75) Inventors: Christopher W. Grote, Webster Groves, MO (US); Joseph P. McClurg, Manchester, MO (US); John E. Johnson, Jr., Maryville, IL (US); Sarah M. Farris, Arnold, MO (US)

(73) Assignee: MALLINCKRODT LLC, Hazelwood, MO (US)

( * ) Notice: Subject to any disclaimer, the term of this patent is extended or adjusted under 35 U.S.C. 154(b) by 125 days.

This patent is subject to a terminal disclaimer.

(21) Appl. No.: 13/491,676

(22) Filed: Jun. 8, 2012

(65) Prior Publication Data

US 2012/0316343 A1    Dec. 13, 2012

Related U.S. Application Data

(60) Provisional application No. 61/494,965, filed on Jun. 9, 2011.

(51) Int. Cl.
C07D 221/22 (2006.01)
C07D 221/28 (2006.01)
A61K 31/44 (2006.01)
C07D 471/08 (2006.01)

(52) U.S. Cl.
CPC ............ *C07D 221/28* (2013.01); *C07D 471/08* (2013.01)

(58) Field of Classification Search
CPC ....... C07D 221/22; C07D 21/28; A61K 31/44
See application file for complete search history.

(56) References Cited

U.S. PATENT DOCUMENTS

| | | | |
|---|---|---|---|
| 2,578,787 A | 12/1951 | DeBenneville | |
| 2,772,270 A | 11/1956 | Weiss | |
| 3,717,643 A | 2/1973 | Archer | |
| 4,089,855 A | 5/1978 | Chatterjie et al. | |
| 4,443,605 A | 4/1984 | Kotick et al. | |
| 4,521,601 A | 6/1985 | Rice | |
| 4,673,679 A | 6/1987 | Aungst et al. | |
| 4,775,759 A | 10/1988 | Rice et al. | |
| 4,795,813 A | 1/1989 | Schwartz | |
| 4,912,114 A | 3/1990 | Revesz | |
| 4,991,391 A | 2/1991 | Kosinski | |
| 5,240,933 A | 8/1993 | Merz et al. | |
| 5,336,483 A | 8/1994 | de Costa et al. | |
| 5,668,285 A | 9/1997 | Rice et al. | |
| 5,693,820 A | 12/1997 | Helmchen et al. | |
| 5,756,745 A | 5/1998 | Kavka | |
| 5,847,142 A | 12/1998 | Mudryk et al. | |
| 6,177,438 B1* | 1/2001 | Nagase et al. | 514/280 |
| 6,184,381 B1 | 2/2001 | Ikariva et al. | |
| 6,323,212 B1 | 11/2001 | Nagase et al. | |
| 6,509,467 B1 | 1/2003 | Blacker et al. | |
| 6,887,999 B1 | 5/2005 | Likhotvorik | |
| 7,045,646 B2 | 5/2006 | Tanis et al. | |
| 7,230,134 B2 | 6/2007 | Borner et al. | |
| 8,471,023 B2* | 6/2013 | Grote et al. | 546/74 |
| 8,519,133 B2* | 8/2013 | Grote et al. | 546/44 |
| 2004/0267051 A1 | 12/2004 | Boerner et al. | |
| 2005/0038061 A1 | 2/2005 | Schutz et al. | |
| 2006/0182692 A1 | 8/2006 | Fishburn et al. | |
| 2008/0009629 A1 | 1/2008 | Avdagic | |
| 2008/0045715 A1 | 2/2008 | Mitchell et al. | |
| 2008/0234307 A1 | 9/2008 | Schuetz et al. | |
| 2010/0022774 A1 | 1/2010 | Kvernenes et al. | |
| 2010/0041888 A1 | 2/2010 | Grote et al. | |
| 2010/0081817 A1 | 4/2010 | Hudson et al. | |
| 2010/0197921 A1 | 8/2010 | Grote et al. | |
| 2010/0216995 A1 | 8/2010 | Grote et al. | |
| 2010/0317683 A1* | 12/2010 | Grote | C07D 489/00 514/282 |
| 2010/0317861 A1 | 12/2010 | Grote et al. | |

FOREIGN PATENT DOCUMENTS

| | | |
|---|---|---|
| CN | 1115318 | 1/1996 |
| CN | 101265266 | 9/2008 |
| CN | 101265266 A * | 9/2008 |
| DE | 922827 | 1/1955 |
| EP | 0034480 | 8/1981 |
| EP | 0879823 | 11/1998 |
| JP | 416905 | 4/1966 |
| JP | 417786 | 4/1966 |
| JP | 417787 | 4/1966 |
| WO | 2004085058 | 10/2004 |
| WO | 2005100361 | 10/2005 |
| WO | 2006035195 | 4/2006 |

(Continued)

OTHER PUBLICATIONS

Li, Jx. et al. Synthesis and biological evaluation of unique stereodimers of sinomenine analogues as potential inhibitors of NO production. Bioorganic & Medicinal Chemistry. 2011, vol. 19, p. 3098.*

Noyori, R. et al. Asymmetric Transfer Hydrogenation Catalyzed by Chiral Ruthenium Complexes. Acc. Chem. Res. 1997, vol. 30, p. 99, figure 1, compounds 3, 4, and 9c; p. 101, left column, lines 1-9.*

Noyori, R. et al. Asymmetric Transfer Hydrogenation Catalyzed by Chiral Ruthenium Complexes. Acc. Chem. Res. 1997, vol. 30, p. 99.*

Hori, M. et al. Synthesis and Analgetic Activity of Sulfur-Containing Morphinans and Related Compounds. Chem. Pharm. Bull. 1989, vol. 37, p. 1246.*

Palmer et al., "Asymmetric transfer hydrogenation of C=O and C=N bonds", Tetrahedron: Asymmetry 10, 1999, p. 2045-2061, XP 004174087.

Puntener et al., "New Efficient Catalysts for enantioselective Transfer Hydrogenations", Tet. Lett., 1996, 37(45), pp. 8165-8168.

Sagara et al., "Specific Affinity Labeling of . . . ", Bioorganic & Medicinal Chemistry Letters, vol. 5, No. 15 1995, p. 1609-1614.

(Continued)

*Primary Examiner* — Rita Desai
*Assistant Examiner* — Ben S Michelson

(57) ABSTRACT

The present invention provides compositions of 6-amino morphinan compounds and process for their synthesis. In particular, the processes provide for the reductive amination of 6-keto morphinans by catalytic transfer hydrogenation, to produce 6-amino morphinan compounds, which are epimerically and/or diastereomerically enriched.

1 Claim, No Drawings

(56) References Cited

FOREIGN PATENT DOCUMENTS

| WO | 2006052710 | 5/2006 |
|---|---|---|
| WO | 2009012005 | 1/2009 |

OTHER PUBLICATIONS

Saunders et al., "Assessment of relative nutritive value of proteins using *Streptoccus zymogenes*", Chemistry and Industry, Jan. 13, 1968, pp. 56-58.

Sayre et al., "Stereospecific synthesis of the 6a- and 6b-Amino Derivatives of Naltrexone and Oxymorphone", J. Org. Chem., 1980, 45, pp. 3366-3368.

Schellenberg, "The Synthesis of Secondary and Tertiary Amines by Borohydride Reduction", Nov. 1963, p. 3259-3261.

Schmidhammer, "134. Synthesis and Biological ion of 14-Aikoxymorphinans Part 4) Opioid Agonists and Partial Opioid Agonists in a Series of . . . ", Helevitca Chimca Acta, vol. 72, 1989, p. 1233-1239.

Schutz et al., "Synthesis of 6-amino Acid Substituted Derivatives of the Highly Potent Analgesic 14-0-methyloxymorphone", Helvetica Chimica Acta, 2003, 86(6), pp. 2142-2148.

Seki, "Studies on the Morphine Alkaloids . . . ", vol. 84, No. 7, p. 626-631.

Seki, "Studies on the Morphine Alkaloids . . . ", vol. 84, No. 7, p. 626-631, English Translation.

Sheth et al., "Synthesis of N-(3',4'-Dimethoxy-5'-bromophenethyl)-2-(4"-hydrioxyphenyl)-acetamide & Allied Products", Indian Journal of Chemistry, vol. 15B, Jul. 1977, pp. 595-598.

Simon et al., "Stereoselective Synthesis of B~-naltrexol, B~-naloxol, B~-naloxamine, B~-naltrexamine and Related Compounds by the Application of the Mitsunobu Reaction", Tetrahedron, 1994, 50(32), pp. 9757-9768.

Small et al., "The Addition of Organomagnesium Halides to Pseudocodeine Types. IV. Nuclear-Substituted Morphine Derivatives", Contribution from the Cobb Chemical Laboratory, University of Virginia, Received Jun. 6, 1938, pp. 204-232.

Spadoni et al., "2-[N-Acylamino(C,-C3)alkyl)indoles as MT, . . . ", J. Med. Chem., 1998, 41, p. 3624-3634.

Tolkachev et al., "Synthetic Investigation in [Kurarealkaloidov] Area XVI. Synthesis 1-(e'-Bromine . . . ", Organicheskoi Khimii, 1966, 36(10), pp. 1767-1772.

Tolkachev et al., "Synthetic Investigation in [Kurarealkaloidov] Area XVI. Synthesis 1-(e'-Bromine . . . ", Organicheskoi Khimii, 1966, 36(10), pp. 1767-1772, English Translation provided by FAST-TRANS.

Uba et al,, "Stereospecific Synthesis of Codeine . . . ", Chem. Pharm. Bull., vol. 27, Issue 9, 1979, p. 2257-2258.

Uematsu et al., "Asymmetric Transfer Hydrogenation of Imines", J. Am. Chem. Soc., 1996, 118, p. 4916-4917.

Uwai et al., "Syntheses and receptor-binding studies of derivatives . . . ", Bioorganic & Medicinal Chemistry, 12,2004, p. 417-421, XP 002488979.

H.C. van der Plas et al., "On the reaction of 2-, 3- and 4-bromo(chloro)-1,8-naphthyridine with potassium amide in liquid ammonia", Laboratory of Organic Chemistry, Agricultural University, Wagenagen, The Netherlands, (Received Oct. 101, 1977).

Van Gurp et al, "Synthesis of 7,8-Didehydro-3,4-Dimethoxy . . . ", Bull. Soc. Chim. Belg., vol. 96/n° Apr. 1987, p. 325-329.

Venkov et al., "Synthesis of isoquinolines from 2-phenylethylamines, amides, nitriles and carboxylic acids in polyphosphoric acid", Tetrahedron 19960909 GB, vol. 52, No. 37, Sep. 9, 1996, pp. 12299-12308, XP 002476120.

Voronin et al., "Synthetic Investigations in the Field of the Curare Alkaloids XII. Synthesis of Isomeric Tubocurarin Iodides", Chemistry of heterocyclic Compounds, Chemistry of Heterocyclic Compounds, 1967, pp. 447-450 (English Translation of Voronin et al., Khimiya Geterotsiklicheskikh Soedinenii, 1969, 4, pp. 606-610).

Watanabe et al., "Novel Synthesis of the Ortho Ester Derivative of 4,5-Epoxymorphinan", Organic Letters, vol. 8, No. 3, 2006, p. 523-526.

White at al., "Asymmetric Total Synthesis of (+)-Codeine via . . . ", J. Org. Chem., 1999,64, p. 7871-7884.

White et al., "Asymmetric Synthesis of (+)-Morphine . . . ", J. Org. Chem., 1997, 62, p. 5250-5251.

Wu et al., "Asymmetric transfer hydrogenation of imines and iminiums . . . ", Chem. Commun., 2006, p. 1766-1768.

Yamakawa et al., "The Methai-Ligand Bifunctional Catalysis: A Theoretical Study an . . . ", J. Am. Chem. Soc., 2000, 122, p. 1466-1478.

Jiang et al., "Stereochemical Studies of Medicinal Agents. 23. Synthesis and biological Evaluation . . . ", American chemical Society, 20(8), Aug. 1977, XP 001070237.

Takemori et al., "Stereochemical Studies on Medicinal Agents . . . ", Journal of Medicinal Chemistry, 1977, 20(8), pp. 1100-1102.

Reddy et al., "A Convenient Method for the N-formylation of secondary amines . . . ", J Tetrahedron Letters, 41, 2000, pp. 9149-9151.

Brossi, A., Atwell, L, Jacobson, A.E., Rozwadowska, M. D., Schmidhammer. 235. Structure-Activity Relationship Of Oxygenated Morphinans. VII 5-Methylated and 14-Hydroxy-substituted Agonists and Antagonists of the 4-Hydroxy-and 3,4-Dioxygenated 6-Morphinanone Series. Helvetica Chimica Acta. 1982, 65, 2394-2404.

Olieman et al., "Conversion of (-31 )-dihydrocodeinone into . . . ", Laboratory of Organic chemistry Technische Hogeschool Delft, Julianalaan 136, Delft, The Netherlands, Mar. 15, 1976.

Olsen et al., "Conjugate Addition Ligands of Opioid Antagonists . . . ", J. Med. Chem., 1990, 33(2), p. 737-741.

Abdel-Magid et al., "Reductive Animation of Aldehydes and Ketones . . . ", Tetrahedron Letters, vol. 31, No. 39, 1990, p. 5595-5598.

Beyerman at al., "Synthesis of racemic and optically active codeine and morphine via the Nformylnordihydrothebainones", Journal of the Royal Netherlands Chemical Society, 97, 5, May 1978, p. 127-130.

Beyerman et ai., "Synthesis of racemic and of (+)-and (-31 )-1 methyldihydrothebainone. (Chemistry of opium alkaloids, Part IV)", Reel. Tray. Chim. Pays-Bas, 1976,75, p. 184-188.

Bognar et al., Izvestiya po Khimiya, 1975, 81(1), p. 203-215.

Borch et al., "The cyanohydridoborate Anion as a Selective Reducing Agent", Journal of the American Chemical Society, 93:12, Jun. 16, 1971, p. 2897-2904.

Borch et al., "A New Method for the Methylation of Amines", J. Org, Chem., vol. 36, No. 10, 1972, pp. 1673-1674.

Brine et al., "Formamidinesulfinic Acid Reduction of Dihydrocodeinone Derivatives", J. Org. Chem., vol. 43, No. 8 1978, p. 1555-1557.

Burke et al., "Probes for narcotic Receptor Mediated Phenomena . . . ", Heterocycles, vol. 23, No. 1, 1985, p. 99-110.

Butora et al., "Chemoenzymatio Synthesis of the Morphine Skeleton via Radical . . . ", Tetrahedron Letters, vol. 37, No. 45, 1996, p. 8155-8158.

Campbell et al., The Preparation of Unsymmetrical Secondary Aliphatic Amines, Jan. 1944, vol. 66, p. 82-84.

Chatterjie et al., "Reduction of6-Ketones of the Morphine Series . . . ", J. Org. Chem., vol. 41, No. 22, 1976, p. 3624-3625.

De Benneville et al., "The Behavior of aliphatic Aldehydes in the Leuckart-Wallach Reaction", J. Am. Chem. Soc., 1950, 72, pp. 3073-3075.

De Costa et al., "Probes for Narcotic Receptor Mediated Phenomena . . . ", J. Med. Chem., 19972, 35, p. 2826-2835.

Farber et al., "A Synthesis of Armepavine and Related Bases. Resolution of (±)-Armepavine",Anales. Asoc. Quim. Argentina, 58, 1970, pp. 133-138.

Farber et al., "Resolution of (±)-armepavine", Chemistry and Industry, Jan. 13, 1968, pp. 57-58.

Fuiji et al., "The First Example of the Stereoselective Synthesis of . . . ", Chem. Pharm. Bull., 52(6), 2004, p. 747-750.

Fuiji et al., "Ruthenium(II)-Caatalyzed Asymmetric Transfer . . . ", J. Am. Chem. Soc., 1996, 118, p. 2521-2522.

Gao et al., "Synthesis of 7-Arylmorphinans . . . ", J. Med. Chem., 1998, 41, p. 3901-3098.

Gorlitzer et al., "Diepoxy-bis-(iminoethano)-dinaphth[2, 1-b:1 ',2'-i]acridine, 2,3)", Arch. Pharm. (Weinheim) 325, 1992, p. 637-641.

(56) References Cited

OTHER PUBLICATIONS

Greene et al., "Protection for Phenols", Protective Groups in Organic Synthesis, 3rd, Ed., c1999, pp. 249-257 and 266-269.
Gribble et al., "Reactions of Sodium Borohydride in Acidic Media . . .", Communications, Aug. 1987, p. 709-711.
Hashiguchi et al, "Asymmetric Transfer Hydrogenation of Aromatic ketones Catalyzed by chiral Ruthenium(II) Complexes", J. Am. Chem. Soc., vol. 177, No. 28, 1995, p. 7562-7563.
Huang et al., "Synthesis of (+−)-Giaucine and (+−)-Neospirodienone via an One-Pot Bischler-Napieralski Reaction and Oxidative Coupling by a Hypervalent Iodine Reagent", Helvetica chimica Acta 2004 CH, vol. 887, No. 1, 2004, pp. 167-174, XP002476119.
Kalimin et al., "Palladium-Catalyzed 2-Phenylethenylation of Codeine . . .", Helevetica Chimca Acta, vol. 89, 2006, p. 861-869.
Kametani et al., "131. Coclaurine 7 -Benzyloxy-1,2,3,4-tetrahydro-1-(p-hydroxyphenyI)-6-methoxy-2-methylisoquinoline    7 -Benzyloxy-1 ,2,3,4-tetrahydro-1-(p-hydroxybenzyI)-6-methoxy-2-methylisoquinoline", Coclaurine, vol. 87, No. 7, 1967, pp. 757-760.
Kametani et al., "131. Coclaurine 7-Benzyloxy-1,2,3,4-tetrahydro-1-(p-hydroxypheny1)-6-methoxy-2-meihylisoquinoline 7-Benzyloxy-1,2,3,4-tetrahydro-1-(p-hydroxybenzyI)-6-methoxy-2-methylisoquinoline", Coclaurine, vol. 87, No. 7, 1967, pp. 757-760, English Translation.
Kashdan et al., "Synthesis of 1,2,3,4-Tetrahydroisoquinolines", J. Org. Chem., 1982, 47, pp. 2638-2643.
Kirby et al., "Synthesis of 14B-Mercaptocodeine Derivatives from N-t-Butoxycarbonyl-N-northebaine", Journal of chemical Research. Miniprint., 1984 pp. 2073-2086, XP9127313.
Kitamura et al., "General Asymmetric Synthesis of Isoquinoline Alkaloids. Enantioselective Hydrogenation of Enamides Catalyzed by Binap-Ruthenium(II) Complexes", J. Org. Chem., 1994, 59, p. 297-310.
Klunenberg et al., "A Remarkable Influence of the Electrolyte in Andoic cyclization of 1-Benzyltetrahydroisoquinolines to neospirodienones or Morphinandienones", Tetrahedron Letters, 1982, vol. 23, No. 44, pp. 4581-4584.
Koolpe et al., "Opioid Agonists and Antagonists, 6-Desoxy-6-substituted . . .", J. Med. Chem., 1985, 28(7), p. 949-957.
Lau et al., "Evolutiion of a Series of Non-Quinoline Leukotriene D4 Receptor Antagonist . . . ", Bioorganic & Medicinal chemistry Letters, vol. 5, No. 15, 1995, p. 1615-1620.
Lazaret al., "A Selective Removal of Benzyl Protecting Groups in Arylphosphate Esters with Bromotrimethylsilane", Synthetic Communications, 22(6), 1992, p. 923-931.

Leland et al., "Analgesic narcotic antagonists. 5. 7,7-Dimethyldihydrocodeinones . . . ", J. Med. Chem., 1981, 24, PQ. 717-721.
Lespagnol et al., "Preparation d'amides de l'homoveratrylamine et d'acids iodophenylacetiques substitutes", Chim. Therap., 1965, pp. 14-16.
Lespagnol et al., "Preparation of amides from the homoveratrylamine and iodephenylacetic substituted acids", Chim. Therap., 1965, pp. 14-16, English Translation by FAST-TRANS.
Malspeis at al., "Metabolic Reduction of Naltrexone I. Synthesis, Separation . . . ", Res. Commun. Cherm. Pathol. Pharmacol, 2(43), 1975.
Mao et al., "A Chiral Rhodium Complex for Rapid Asymmetric Transfer . . . ", Organic Letters, 1999, vol. 1, No. 6, p. 841-843.
Meuzelaar et al., "Chemistry of Opium Alkaloids, 45 Improvements in the Total Synthesis of Morphine", Eur. J. Org. Chem., 1999, pp. 2315-2321.
Mohamed et al., "Stereoselectivity of the Reduction of Naltrexone Oxime with Borane", Journal of Organic chemistry, 1986, 51(1), pp. 105-106.
Nagase at al., "The Facility of Formation of a Bond in Dihydromorphinone and Related Opiates", J. Org. Chem., 1989, 54, PQ. 4120-4125.
Nagata et al., "Synthetic Studies on Isoquinoline Alkaloids. I. An Efficient Synthesis of 9,10-Substituted Protoberberine Alkaloids" Chem. Pharm. Bull., 194, 23(11), pp. 2867-2877.
Noyori et al., "Asymmetric Catalysts by Architechtural and Functional Molecular . . . ", Agew. Cherm. Int., Ed. 2001, 40, p. 40-73.
Noyori et al "Asymmetric Transfer Hydrogenation Catalyzed by Chiral Ruthenium Complexes", Ace. Chem. Res., 1997, 30, pp. 97-102.
Ohno et al., "Solid-Phase synthesis of 6-Sulfionylamino Morphinan Libraries", Synlett, 2002, No. 1, p. 93-96.
Olfoson et al., "A New Reagent for the Selective, High-Yield N-Dealkylation of Teritary Amines: Improved Syntheses of Naltrexone and Nalbuphine", J. Org. Cherm., 1984, 49, p. 2081-2082.
Teng, et al., "Synthesis and biological evaluation of unique stereodimers of sinomenine analogues as potential inhibitors of NO production," Bioorganic & Medicinal Chemistry, vol. 19, No. 10, pp. 3096-3104 (Apr. 4, 2011).
Vedejs, E., Substituted Isoquinolines by Noyori Transfer Hydrogenation: Enantioseleotive Synthesis of Chiral Diamines Containing an Aniline Subunit. Journal of Organic Chemistry. 1999, 64, 6724-6729.

* cited by examiner

REDUCTIVE AMINATION OF 6-KETO MORPHINANS BY CATALYTIC HYDROGEN TRANSFER

CROSS REFERENCE TO RELATED APPLICATIONS

This application claims the benefit of U.S. Provisional Application No. 61/494,965 filed Jun. 9, 2011, which is incorporated herein in its entirety.

FIELD OF THE INVENTION

The present invention generally relates to compositions comprising 6-amino morphinan compounds, wherein the 6-amino morphinan is lacking the 4,5-epoxy ring. The invention also relates to processes for the production of the 6-amino morphinan compounds. These processes encompass the reductive amination of a 6-keto morphinan compound to produce 6-amino morphinan, wherein both morphinan compounds lack the 4,5-epoxy ring. Another aspect of the invention relates to compositions of the 6-amino morphinan compounds and intermediates which are diastereomerically or epimerically enriched and the processes for making 6-amino compounds and intermediates that are diastereomerically or epimerically enriched.

BACKGROUND OF THE INVENTION

Morphinans are important pharmaceuticals that typically are used as analgesics or drug/alcohol cessation agents. Substituted morphinans, such as 6-amino derivatives, may be useful therapeutically because they have higher efficacy, greater potency, and/or may function as prodrugs. Moreover, the potency of particular morphinan compounds may be increased by particular configurations at the chiral centers of the compounds. Although several methods for forming 6-amino morphinans from 6-keto morphinans have been reported in the literature, none provides the selective synthesis of 6-amino morphinans, wherein the morphinan compounds lack the 4,5-epoxy ring, which produces particular epimers and diastereomers in good yield. There is a need, therefore, for simple, mild, and efficient processes for the preparation of these diastereomerically or epimerically enriched 6-amino morphinans.

SUMMARY OF THE INVENTION

The present invention provides compositions of 6-amino morphinan compounds wherein the morphinans are lacking a 4,5-epoxy ring. The invention further provides processes for forming the 6-amino morphinan compounds lacking the 4,5-epoxy ring. The processes also provide for epimerically or diastereomerically enriched 6-amino morphinan compounds lacking the 4,5-epoxy ring.

One aspect of the present invention encompasses a process for preparing a 6-amino morphinan. The process comprises contacting a 6-keto-morphinan with an amine source, a transition metal catalyst, and a proton donor comprising an anion, and a proton acceptor to produce the 6-amino morphinan, wherein the 6-keto and 6-amino morphinan lack the 4,5-epoxy ring.

Another aspect of the invention provides a process for preparing a compound comprising Formula (IV):

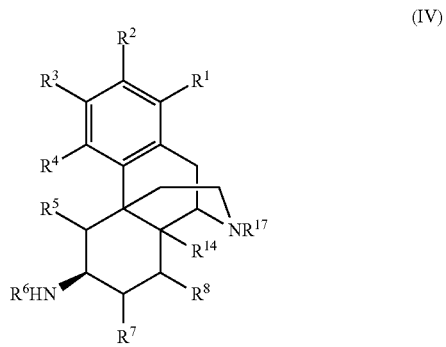

The process comprises reducing a compound comprising Formula (I) in the presence of an amine source ($R^6NH_2$), a transition metal catalyst, a hydrogen donor comprising an anion (X), and a proton acceptor to form the compound comprising Formula (IV). The compound of Formula (I) comprises:

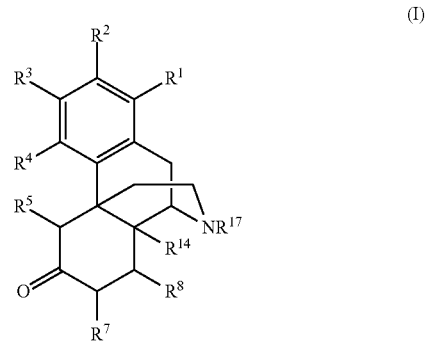

For each of the compounds comprising Formulas (I) or (IV), the variables stand for the following:

$R^1$, $R^2$ and $R^5$ are chosen from hydrogen, hydrocarbyl, substituted hydrocarbyl, halogen, and $\{-\}OR^{15}$;

$R^3$ and $R^8$ are chosen from hydrogen, hydrocarbyl, substituted hydrocarbyl, and $\{-\}OR^{15}$;

$R^4$ is are chosen from hydrogen, hydrocarbyl, substituted hydrocarbyl, $\{-\}OR^{15}$;

$R^6$ is chosen from hydrocarbyl or substituted hydrocarbyl;

$R^7$ is chosen from hydrocarbyl, substituted hydrocarbyl, and $\{-\}OR^{15}$;

$R^{14}$ is chosen from hydrogen and $\{-\}OR^{15}$;

$R^{15}$ is chosen from hydrogen, hydrocarbyl, substituted hydrocarbyl, and a hydroxy protecting group; and $R^{17}$ is chosen from hydrocarbyl, substituted hydrocarbyl, and protecting group.

A further aspect of the invention encompasses a composition comprising a compound comprising Formula (IV) less than about 15% of a 6-alpha-amino epimer of the compound comprising Formula (IV):

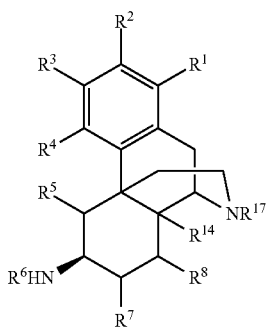

(IV)

wherein:
R¹, R², and R⁵ are chosen from hydrogen, hydrocarbyl, substituted hydrocarbyl, halogen, and {—}OR¹⁵;
R³ and R⁸ are chosen from hydrogen, hydrocarbyl, substituted hydrocarbyl, and {—}OR¹⁵;
R⁴ is chosen from hydrogen, hydrocarbyl, substituted hydrocarbyl, and {—}OR¹⁵;
R⁶ is chosen from hydrocarbyl and substituted hydrocarbyl;
R⁷ is chosen from hydrocarbyl, substituted hydrocarbyl, and {—}OR¹⁵;
R¹⁴ is chosen from hydrogen and {—}OR¹⁵;
R¹⁵ is chosen from hydrogen, hydrocarbyl, substituted hydrocarbyl, and a hydroxy protecting group; and
R¹⁷ is chosen from hydrocarbyl, substituted hydrocarbyl, and protecting group.

Yet another aspect of the invention encompasses the intermediate compound comprising Formula (III) and less than about 15% of a 6-alpha-amino epimer of the compound comprising Formula (III):

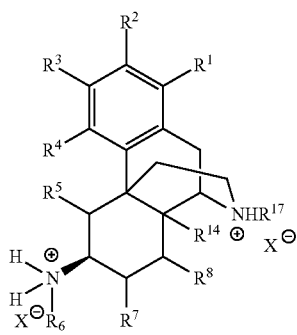

(III)

wherein:
R¹, R² and R⁵ are hydrogen, hydrocarbyl, substituted hydrocarbyl, halogen, and {—}OR¹⁵;
R³ and R⁸ are chosen from hydrogen, hydrocarbyl, substituted hydrocarbyl, and {—}OR¹⁵;
R⁴ is are chosen from hydrogen, hydrocarbyl, substituted hydrocarbyl, and {—}OR¹⁵;
R⁶ is chosen from hydrocarbyl and substituted hydrocarbyl;
R⁷ is chosen from hydrocarbyl, substituted hydrocarbyl, and {—}OR¹⁵;
R¹⁴ is chosen from hydrogen and {—}OR¹⁵;
R¹⁵ is chosen from hydrogen, hydrocarbyl, substituted hydrocarbyl, a hydroxy protecting group;

R¹⁷ is chosen from hydrocarbyl, substituted hydrocarbyl, and protecting group; and
X is an anion.

Other features and iterations of the invention are described in more detail below.

DETAILED DESCRIPTION OF THE INVENTION

The present invention provides compositions of 6-amino morphinan compounds, salts, intermediates, or analogs thereof, wherein the morphinan compounds lack a 4,5-epoxy ring. Further provided are processes for the synthesis of the 6-amino morphinan compounds, where the processes further provide for production of the 6-amino morphinan compounds with a diastereomeric or epimeric enrichment. The process involves the transformation of a 6-keto moiety of a morphinan to a 6-amino moiety by reductive amination in a transfer hydrogenation environment. Specifically, the 6-keto moiety of the morphinan compound is condensed with an amine source in the presence of a transition metal catalyst, a hydrogen donor comprising an anion, and a proton acceptor. The processes also provide the product 6-amino morphinan with an enrichment of diastereomers or epimers. Additionally, the processes of the invention avoid the use of hydrogen gas and highly reactive main group reducing agents. Accordingly, the processes are mild and tolerate many functional groups that may be reduced in the presence of a more active reducing agent. Advantageously, the processes of the invention provide the compounds with epimeric and diastereomeric enrichments.

(I) Processes for the Preparation of 6-Amino Morphinans

One aspect of the invention encompasses processes for the syntheses of 6-amino morphinans. The processes comprise contacting a 6-keto morphinan with an amine source, a hydrogen donor comprising an anion, a transition metal catalyst, and a proton acceptor to form a 6-amino morphinan.

The core morphinan structure of the 6-keto morphinan starting material contains at least three stereo centers at the 9-, 13-, and 14-positions. The configuration of these positions may be either R or S, such that C-15 and C-16 of the N-ring structure are either both on the alpha side of the molecule, or both on the beta side of the molecule. By alpha and beta it is meant, respectively, in with respect to the plane which the compound is drawn, and out with respect to the plane as the compound as drawn. The core morphinan structure and the numbering are shown below.

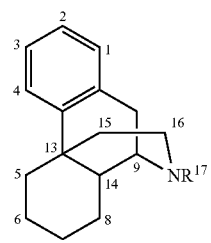

Contact of the 6-keto moiety with the amine source, the transition metal catalyst, and the hydrogen donor leads to formation of an intermediate compound, i.e., a salt of 6-imine morphinan. The imine moiety of the intermediate is converted in situ to the 6-amino morphinan. The transformation from a ketone or imine moiety to an amine moiety also represents a transformation of a sp² carbon to a sp³ configuration, such that the C-6 of the 6-amino morphinan may have a configuration of alpha or beta.

(II) Processes for the Preparation of Compounds Comprising Formula (IV)

In one embodiment of the invention, a compound comprising Formula (IV) is prepared from a compound comprising Formula (I). The process comprises reducing the compound comprising Formula (I) in the presence of an amine source ($R^6NH_2$), a hydrogen donor comprising an anion (X), and a transition metal catalyst, wherein an intermediate compound comprising Formula (II) is formed. The compound comprising Formula (II) is converted in situ to a compound comprising Formula (III). The process further comprises contacting the compound comprising Formula (III) with a proton acceptor to form the compound comprising Formula (IV). For purposes of illustration, Reaction Scheme 1 depicts the synthesis of the compound comprising Formula (IV) in accordance with one aspect of the invention:

Reaction Scheme 1

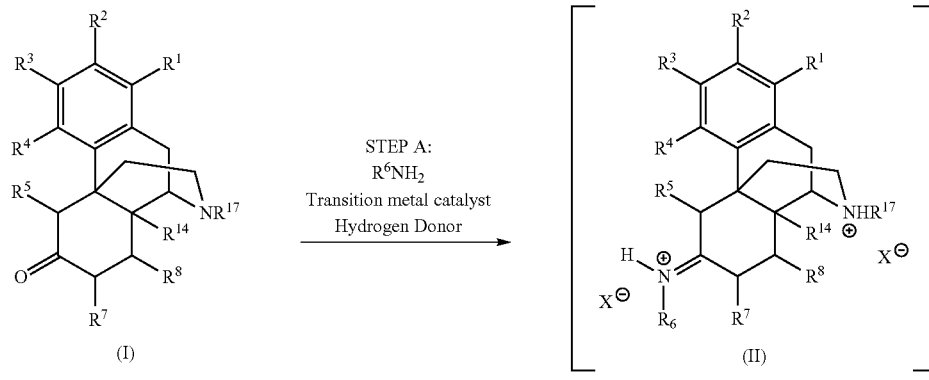

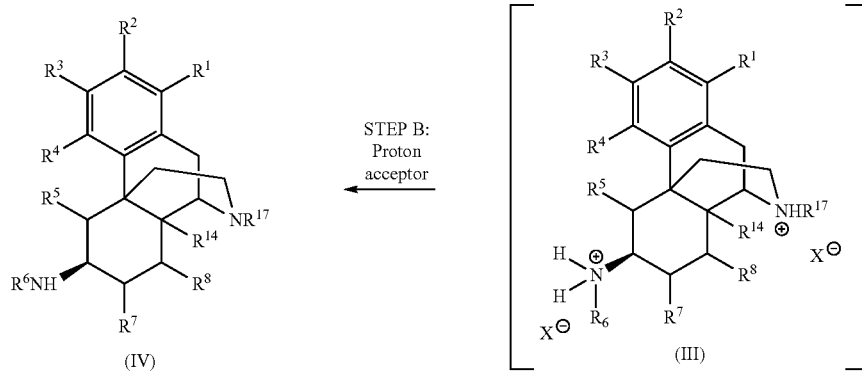

wherein:
R$^1$, R$^2$ and R$^5$ are hydrogen, hydrocarbyl, substituted hydrocarbyl, halogen, and {—}OR$^{15}$;
R$^3$ and R$^8$ are chosen from hydrogen, hydrocarbyl, substituted hydrocarbyl, and {—}OR$^{15}$;
R$^4$ is are chosen from hydrogen, hydrocarbyl, substituted hydrocarbyl, and {—}OR$^{15}$;
R$^6$ is chosen from hydrocarbyl and substituted hydrocarbyl;
R$^7$ is chosen from hydrocarbyl, substituted hydrocarbyl, and {—}OR$^{15}$;
R$^{14}$ is chosen from hydrogen and {—}OR$^{15}$;
R$^{15}$ is chosen from hydrogen, hydrocarbyl, substituted hydrocarbyl, a hydroxy protecting group;
R$^{17}$ is chosen from hydrocarbyl, substituted hydrocarbyl, and protecting group; and
X is an anion.

In some embodiments, R$^1$, R$^2$, R$^5$, and R$^8$ are hydrogen; R$^3$ and R$^4$ are independently chosen from alkoxy, hydroxy, and protected hydroxyl; R$^{14}$ is hydrogen or hydroxyl; and R$^{17}$ is chosen from alkyl, cycloalkyl, cycloalkylmethyl, alkynyl, aryl and heterocyclo. In other embodiments, R$^7$ is chosen from alkoxy and hydroxy. In yet another embodiment R$^7$ is chosen from alkoxy and hydroxy and R$^6$ is hydrogen, alkyl, substituted alkyl, alkenyl, substituted alkenyl, aryl, and substituted aryl. In one preferred embodiment, each of R$^1$, R$^2$, R$^4$, R$^5$, and R$^8$ are hydrogen; and R$^3$ and R$^7$ are {—}OCH$_3$; and R$^4$ is {—}OH, R$^{14}$ is H, R$^{17}$ is CH$_3$, and C-6 is primarily beta as shown below.

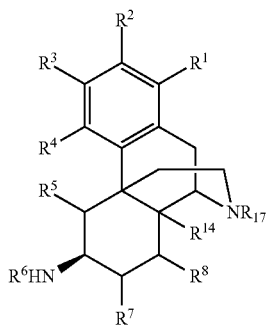

(a) Step A of the Process

The process commences with the formation of a reaction mixture by combining a 6-keto morphinan comprising Formula (I) with an amine source, a hydrogen donor comprising X, and a transition metal catalyst, wherein the compound comprising Formula (I) undergoes reductive amination. A variety of compounds comprising Formula (I) are suitable for use in the process.

In one aspect of the invention, the compound comprising Formula (I) is substituted at the 7-position with an alkoxy or hydroxy moiety. As will be appreciated by one of skill in the art, substitution at the 7-position makes the 7-carbon a stereogenic center as it is substituted with four different substituents. The combination of the 6-keto moiety adjacent to the 7-alkoxy or hydroxy substituent has electronic properties such that a significant equilibrium exists at the 7-position between the (R) and the (S) (or alpha and beta) configurations.

In exemplary embodiments, R$^1$, R$^2$, and R$^8$ are each hydrogen; R$^3$, R$^4$ and R$^7$ are independently chosen from hydroxy or methoxy; R$^{14}$ is hydrogen; and R$^{17}$ is CH$_3$. A representative compound comprising Formula (I) includes, but is not limited to, dihydrosinomenine.

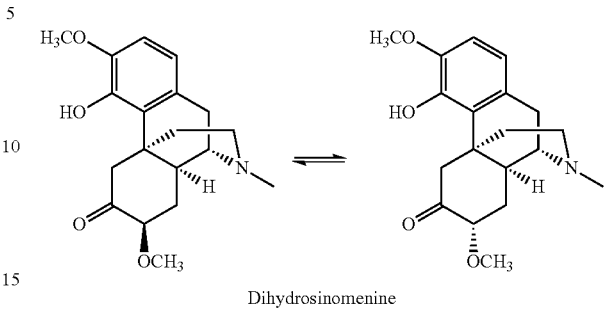

Dihydrosinomenine (i) Amine Source

The reaction mixture also comprises an amine source comprising formula R$^6$NH$_2$, wherein R$^6$ is chosen from hydrogen, hydrocarbyl, and substituted hydrocarbyl. In embodiments in which R$^6$ is hydrogen, the amine source, ammonia (NH$_3$), is provided by an ammonium salt. The ammonium salt may comprise an inorganic anion or an organic anion. Non-limiting examples of suitable inorganic anions include bicarbonate, carbonate, chloride, hydroxide, nitrate, phosphate, sulfide, and sulfate. Examples of suitable organic anions include, but are not limited to, benzoate, butanoate, acetate, citrate, formate, fumarate, glutamate, lactate, malate, propionate, oxalate, succinate, and tartarate. In a preferred embodiment, the ammonium salt is ammonium acetate.

In embodiments in which R$^6$ is hydrocarbyl or substituted hydrocarbyl, the amine source may be a primary amine or an amino ester. In preferred embodiments, R$^6$ is alkyl, substituted alkyl, alkenyl, substituted alkenyl, alkynyl, substituted alkynyl, aryl, heteroaryl, carbocyclic, or heterocyclic. Non-limiting examples of suitable primary amines include methylamine, ethylamine, isopropylamine, propyl amine, allylamine, n-benzylamine, aniline, methanolamine and ethanolamine. Suitable amino esters include, but are not limited to, alanine, the methyl ester of alanine, and glycine.

The molar ratio of the compound comprising Formula (I) to the amine source can and will vary. The molar ratio of the compound comprising Formula (I) to the amine source may range from about 1:1 to about 1:20. In some embodiments, the molar ratio of the compound comprising Formula (I) to the amine source typically will range from about 1:1 to about 1:5. In various embodiments, the molar ratio of the compound comprising Formula (I) to the amine source may range from about 1:1 to about 1:2, from about 1:2 to about 1:3, or from about 1:3 to about 1:5. In an exemplary embodiment, the molar ratio of the compound comprising Formula (I) to the amine source may range from about 1:1.25 to about 1:2.

(ii) Hydrogen Donor

In addition to the compound comprising Formula (I) and the amine source, the reaction mixture also comprises a hydrogen donor comprising X, wherein X is an anion. In general, the anion is formate. Suitable hydrogen donors comprising a formate ion include formic acid, salts of formic acid, wherein the salt may be an organic salt or an inorganic salt, and a mixture of formic acid and an organic base. Suitable inorganic formate salts include, but are not limited to, calcium formate, cesium formate, lithium formate, magnesium formate, potassium formate, and sodium formate. Non-limiting examples of suitable organic salts of formic acid include ammonium formate, ethyl formate, methyl formate, amine formate, butyl formate, propyl formate, triethyl orthoformate, triethyl orthoformate, triethylammonium formate, trimethylammonium formate, and the like. Suitable organic bases for combining with formic acid include, but are not limited to, pyridine, triethylamine, diisopropylethylamine, N-methylmorpholine, and N,N-dimethylaminopyridine. In an exemplary embodiment, the hydrogen donor comprises a mixture of formic acid and an organic base, wherein the organic base is triethylamine.

The molar ratio of the compound comprising Formula (I) to the hydrogen donor comprising X can and will vary. In general, the molar ratio of the compound comprising Formula (I) to the hydrogen donor comprising X will range from about 1:1 to about 1:20. In various embodiments, the molar ratio of the compound comprising Formula (I) to the hydrogen donor comprising X may range from 1:1 to about 1:3, from about 1:3 to about 1:10, or from about 1:10 to about 1:20. In preferred embodiments, the molar ratio of the compound comprising Formula (I) to the hydrogen donor comprising X may range from 1:11 to about 1:13. In exemplary embodiments in which the hydrogen donor comprising X is formic acid and triethylamine, the molar ratio of the compound comprising Formula (I) to triethylamine may range from about 1:1 to about 1:15, or more preferably from about 1:3 to about 1:15. In some embodiments, the hydrogen donor comprising X may be slowly introduced into the reaction mixture. For example, the hydrogen donor comprising X may be added in small aliquots or drops to the reaction mixture.

(iii) Transition Metal Catalyst

The reaction mixture also comprises a transition metal catalyst. The transition metal may be ruthenium, osmium, rhodium, iridium, palladium, or platinum. In a preferred embodiment, the transition metal may be ruthenium, iridium, or rhodium. The valence state of the transition metal may vary. For example, non-limiting examples of suitable transition metals include ruthenium(II), ruthenium(III), ruthenium(IV), osmium(II), osmium(III), osmium(IV), rhodium(I), rhodium(III), iridium(III), iridium(IV), palladium(II), palladium(IV), platinum(II), and platinum(IV).

The transition metal may further exist as a complex with at least one ligand. Typically, the ratio of metal to ligand in the complex is about 1:1. The ligand of the catalytic transition metal complex may be a mono- or bidentate nitrogen donor, a phosphorous donor ligand, a cyclopentadienyl ligand, an arene ligand, an olefin ligand, an alkyne ligand, a heterocycloalkyl ligand, a heteroaryl ligand, a hydride ligand, an alkyl ligand, or a carbonyl ligand.

In preferred embodiments, the catalytic transition metal complex may be dichloro(arene)Ru(II) dimer, dichloro(pentamethylcyclopentadienyl)Rh(II) dimer, BINAP-Ru(II) diacetate, BINAP-Ru(II) dichloride, BINAP-Ru(II) dibromide, BINAP-Ru(II)diiodide, [RuCl((R or S)BINAP)($C_6H_6$)]Cl, dichloro(pentamethylcyclopentadienyl)iridium(III) dimer, Ru(III) chloride, $RuCl_3$ hydrate, Ru(III) acetylacetonate, tetraalkylammonium $RuCl_4$, or pyridinium $RuCl_4$. In an exemplary embodiment, the transition metal catalyst may be dichloro(p-cymene)Ru(II) dimer.

In other embodiments, the catalytic transition metal complex may be an asymmetric catalyst in which at least one metal is complexed with at least one bidentate, ligand using nitrogen, oxygen, or phosphorous donor atoms. These catalysts are sometimes referred to as Noyori catalysts, and are more fully described in, for example, U.S. Pat. No. 5,693,820 (Helmchen et al.) and R. Noyori et al., *Asymmetric Catalysts by Architechtural and Functional Molecular Engineering: Practical Chemo-and Stereoselective Hydrogenation of Ketones*, Agew. Chem. Int. Ed. 2001, 40, pp. 40-73. In one example, the chiral ligand may comprise Formula (670), (680), (690), or (700), as shown below,

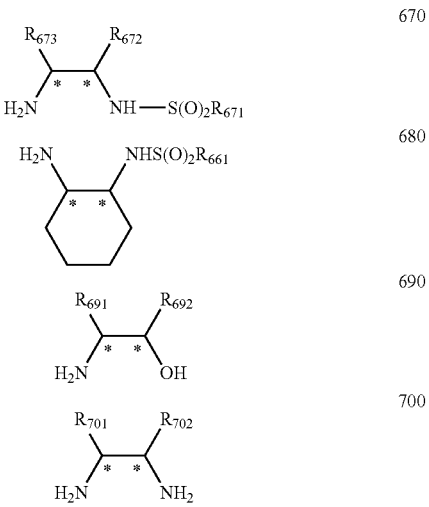

wherein $R_{671}$, $R_{672}$, $R_{673}$, $R_{681}$, $R_{691}$, $R_{692}$, $R_{701}$, and $R_{702}$ are independently alkyl or aryl and wherein $R_{691}$ and $R_{692}$ of Formula (690) and $R_{701}$ and $R_{702}$ of Formula (700), and the carbon atoms to which they are attached, may optionally form a cyclic or bicyclic compound. In the above structures, the "*" indicates a chiral carbon atom. The configuration of the chiral carbons of the asymmetric catalyst having two chiral centers may be RR, RS, SR, or SS.

In one embodiment, the ligand comprises Formula (670) and $R_{672}$ and $R_{673}$ are each phenyl and $R_{671}$ is aryl. In another example of this embodiment, $R_{671}$ is tolyl, mesityl, or naphthyl. In an alternative embodiment, the ligand comprises Formula (680) and $R_{681}$ is tolyl, mesityl, 2,4,6-triisopropylphenyl, or naphthyl. In another example, the ligand comprises Formula (690) and $R_{691}$ and $R_{692}$ are hydrogen thus forming the compound, aminoethanol.

In another embodiment, the ligand corresponds to Formula (700) and $R_{701}$ and $R_{702}$ are hydrogen thus forming the compound, ethylenediamine.

In a preferred example, the chiral ligand may be p-toluenesulfonyl-1,2-diphenylethylenediamine, (1S,2S)-(+)-N-4-toluenesulfonyl-1,2-diphenylethylene-1,2-diamine, (1R,2R)-(−)-N-4-toluenesulfonyl-1,2-diphenylethylene-1,2-diamine, dl-N-tosyl-1,2-diphenylethylenediamine, N-tosyl-1,2-diphenylethylenediamine, N-tosyl-1,2-ethylenediamine, or N-tosyl-1,2-diaminocyclohexane.

Suitable ruthenium or rhodium asymmetric catalysts include the following:

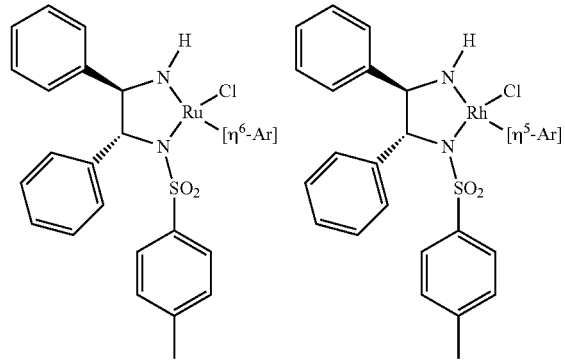

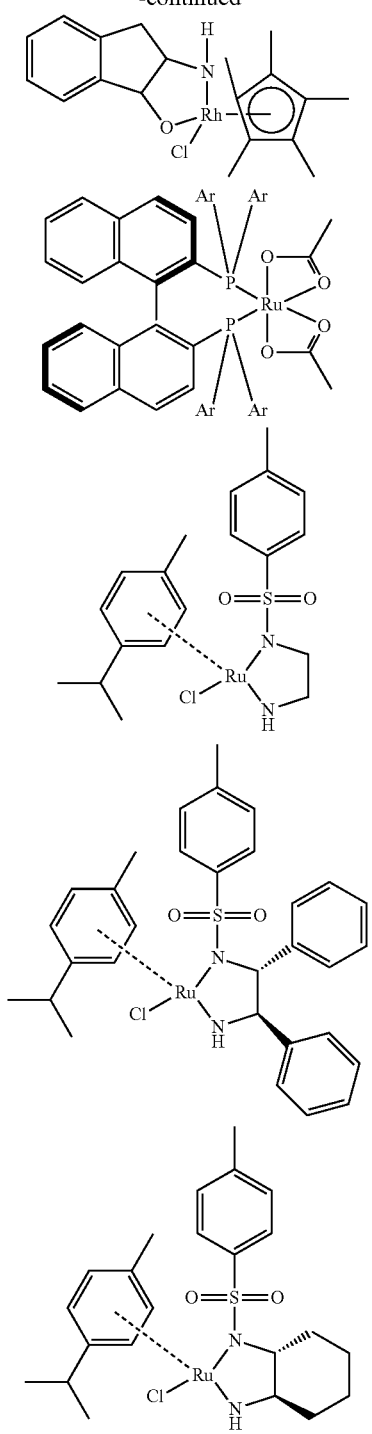

The molar ratio of the compound comprising Formula (I) and the transition metal catalyst complex can and will vary depending, for example, on the nature of the catalyst. In general, the molar ratio of the compound comprising Formula (I) and the transition metal catalyst complex will range from about 1:0.0001 to about 1:0.01. In some embodiments, the molar ratio of the compound comprising Formula (I) and the transition metal catalyst complex may range from about 1:0.0001 to about 1:0.001, or more preferably from about 1:0.001 to about 1:0.01.

(iv) Solvent

The reaction mixture, as detailed herein, may also comprise a solvent. The solvent can and will vary depending on the starting substrate and the reactants used in the process. The solvent may be a protic solvent, an aprotic solvent, a non-polar solvent, or combinations thereof. Suitable examples of protic solvents include, but are not limited to, methanol, ethanol, isopropanol, n-propanol, isobutanol, n-butanol, s-butanol, t-butanol, and combinations thereof. Non-limiting examples of suitable aprotic solvents include acetonitrile, diethoxymethane, N,N-dimethylacetamide (DMAC), N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, 1,4-dioxane, N-methyl-2-pyrrolidinone (NMP), ethyl formate, formamide, hexamethylphosphoramide, N-methylacetamide, N-methylformamide, methylene chloride, nitrobenzene, nitromethane, propionitrile, sulfolane, tetramethylurea, tetrahydrofuran (THF), 2-methyl tetrahydrofuran, trichloromethane, and combinations thereof. Suitable examples of non-polar solvents include, but are not limited to, alkane and substituted alkane solvents (including cycloalkanes), aromatic hydrocarbons, esters, ethers, combinations thereof, and the like. Specific non-polar solvents that may be employed, include, for example, benzene, butyl acetate, t-butyl methylether, chlorobenzene, chloroform, chloromethane, cyclohexane, dichloromethane, dichloroethane, diethyl ether, ethyl acetate, diethylene glycol, fluorobenzene, heptane, hexane, isopropyl acetate, methyltetrahydrofuran, pentyl acetate, n-propyl acetate, tetrahydrofuran, toluene, and combinations thereof. Exemplary solvents include acetonitrile, chloroform, dichloromethane, N,N-dimethylacetamide, N,N-dimethylformamide, N-methyl-2-pyrrolidinone, ethyl acetate, ethanol, and methanol. In embodiments in which the amine source is a primary amine, a preferred solvent is acetonitrile.

In general, the weight ratio of the solvent to the compound comprising Formula (I) will range from about 0.5:1 to about 100:1. In various embodiments, the weight ratio of the solvent to the compound comprising Formula (I) may range from 0.5:1 to about 5:1, from about 5:1 to about 25:1, or from about 25:1 to about 100:1. In preferred embodiments, the weight ratio of the solvent to the compound comprising Formula (I) may range from about 2:1 to about 10:1.

(v) Reaction Conditions

In general, the reaction will be conducted at a temperature that ranges from about 20° C. to about 100° C., or more preferably from about 25° C. to about 70° C. In various embodiments, the temperature of the reaction may be about room temperature (~23° C.), about 30° C., about 40° C., about 50° C., about 60° C., or about 70° C. The reaction may be performed at more than one temperature throughout the processes. The reaction typically is performed under ambient atmosphere and pressure.

Generally, the reaction is allowed to proceed for a sufficient period of time until the reaction is complete, as determined by any method known to one skilled in the art, such as chromatography (e.g., HPLC). The duration of the reaction may range from about 12 hours to more than 5 days. In some embodiments, the reaction may be allowed to proceed for 12 hours, 18 hours, 24 hours, 36 hours, 48 hours, 60 hours, 72 hours, or 84 hours. In this context, a "completed reaction" generally means that the reaction mixture contains a significantly diminished amount of the compound comprising Formula (I). Typically, the amount of the compound comprising Formula (I) remaining in the reaction mixture may be less than about 3%, and preferably less than about 1%.

(b) Intermediate Compounds

During step A of the process, the reductive amination of the compound comprising Formula (I) leads to the formation of an intermediate compound comprising Formula (II), as depicted in Reaction Scheme 1. The imine moiety is converted in situ to the 6-amino moiety in a particular configuration. As a consequence, an intermediate comprising Formula (III) is formed, as shown in Reaction Scheme 1.

In embodiments where the 7-position is an alkoxy or hydroxy, the configuration of the 7-position of Formulas (I) and (II) may be in equilibrium due to the electronic properties of the compound. However, with the conversion to Formula (III) no significant equilibrium at the 6- and 7-positions exists, and the configuration of the 7-position may be either R or S.

The compound comprising Formula (III) may precipitate out of the reaction mixture, and may be recovered from the reaction mixture using standard procedures. In some embodiments, the compound comprising Formula OW may be isolated from the reaction mixture using standard procedures known to those of skill in the art including azeotropic drying or filtration.

(c) Step B of the Process

The process may further comprise contacting the compound comprising Formula (III) with a proton acceptor, wherein the compound comprising Formula (IV) is formed. A variety of proton acceptors are suitable for use in this step of the process. In general, the proton acceptor will have a pKa greater than about 9. Suitable proton acceptors having this characteristic include ammonia, borate salts (such as, for example, $NaBO_3$), bicarbonate salts (such as, for example, $NaHCO_3$, $KHCO_3$, $LiCO_3$, and the like), carbonate salts (such as, for example, $Na_2CO_3$, $K_2CO_3$, $Li_2CO_3$, and the like), hydroxide salts (such as, for example, NaOH, KOH, and the like), organic bases (such as, for example, pyridine, methylamine, diethylamine, triethylamine, diisopropylethylamine, N-methylmorpholine, N,N-dimethylaminopyridine), and mixtures of any of the above. In preferred embodiments, the proton acceptor may be ammonia, ammonium hydroxide, potassium hydroxide, or sodium hydroxide. In an exemplary embodiment, the proton acceptor may be ammonia.

Typically, the amount of proton acceptor that is added to the reaction will be sufficient to adjust the pH of the reaction mixture to a value between 9 and 10. Preferably, the pH of the reaction mixture does not exceed 10. In some embodiments, the pH of the reaction mixture may range from about 9.0 to about 9.2, from about 9.2 to about 9.4, from about 9.4 to about 9.6, from about 9.6 to about 9.8, or from about 9.8 to about 10.0. In exemplary embodiments, the pH of the reaction mixture may range from about 9.3 to about 9.6. The proton acceptor may be may be added in small aliquots or dropwise to the reaction mixture until the desired the pH is reached.

The reaction mixture may further comprise a protic solvent. Suitable protic solvents are listed above in section (II)(a)(iv). In exemplary embodiments, the protic solvent may be water.

Typically, the reaction is allowed to proceed at room temperature for a sufficient period of time until the reaction is complete. The compound comprising Formula (IV) may precipitate out of the reaction mixture. Accordingly, the reaction may be complete when no further precipitate is formed. Alternatively, the reaction may be determined complete by any known to those of skill in that, such as chromatography (e.g., HPLC). In this context, a "completed reaction" generally means that the reaction mixture contains a significantly diminished amount of the compound comprising Formula (III) and a significantly increased amount of the compound comprising Formula (IV) compared to the amounts of each present at the beginning of the reaction. Typically, the amount of the compound comprising Formula (III) remaining in the reaction mixture may be less than about 3%, and preferably less than about 1%.

The compound comprising Formula (IV) may be isolated from the reaction mixture using techniques known to those of skill in the art. Non-limiting examples of suitable techniques include precipitation, extraction, evaporation, chromatography, and crystallization.

The yield of the compound comprising Formula (IV) can and will vary. Typically, the yield of the compound comprising Formula (IV) will be at least about 60%. In one embodiment, the yield of the compound comprising Formula (IV) may range from about 60% to about 80%. In another embodiment, the yield of the compound comprising Formula (IV) may range from about 80% to about 90%. In a further embodiment, the yield of the compound comprising Formula (IV) may range from about 90% to about 95%. In still another embodiment, the yield of the compound comprising Formula (IV) may be greater than about 95%.

The compound comprising Formulas (IV) may be used as is or it may be converted to another compound using techniques familiar to those of skill in the art. The compound comprising Formulas (IV) may also be converted into a pharmaceutically acceptable salt. Pharmaceutically acceptable cations include metallic ions and organic ions. More preferred metallic ions include, but are not limited to, appropriate alkali metal salts, alkaline earth metal salts, and other physiologically acceptable metal ions. Exemplary ions include aluminum, calcium, lithium, magnesium, potassium, sodium, and zinc in their usual valences. Preferred organic ions include protonated tertiary amines and quaternary ammonium cations including, in part, trimethylamine, diethylamine, N,N'-dibenzylethylenediamine, chloroprocaine, choline, diethanolamine, ethylenediamine, meglumine (N methylglucamine) and procaine. Exemplary pharmaceutically acceptable acids include, without limitation, hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, glucosic acid, glucuronic acid, pyruvic acid, oxalacetic acid, fumaric acid, propionic acid, aspartic acid, glutamic acid, benzoic acid, and the like.

The compound(s) prepared by the processes may be diastereomerically or epimerically enriched in that the final product comprises an amount of a single diastereomer greater than about 30%, or greater than about 40%, or greater than about 50%, or an amount of a single epimer greater than about 75%, or in other embodiments, greater than about 80%, or greater than about 90%. The compounds comprising any of Formula (I), (II), (III), and (IV) may have a (−) or a (+) orientation with respect to the rotation of polarized light. More specifically, each chiral center of the morphinan may have an R or an S configuration. In some embodiments, the compounds described herein have at least five chiral centers C-6, C-7, C-9, C-13, and C-14. The configuration of C-6 may be set to primarily beta while C-7, C-9, C-13, and C-14 may be R or S. Thus, the configurations of C-6, C-7, C-9, C-13, and C-14, respectively, may be SRRRR, SRRRS, SRRSR, SRSRR, SSRRR, SRRSS, SRRSR, SSSRR, SSRRS, SSRSR, SRSRS, SRSSS, SSRSS, SSSRS, SSSSR, SSSSS, RRRRR, RRRRS, RRRSR, RRSRR, RSRRR, RRRSS, RSSRR, RSRRS, RSRSR, RRSRS, RRSSS, RSRSS, RSSRS, RSSSR, or RSSSS, provided that the C-15 and C-16 atoms are both on the alpha face of the molecule or both on the beta face of the molecule. In some embodiments, a single diastereomer may be isolated. In such embodiments, each of the chiral centers of the molecule is set in a particular configuration, R or S. Isolation of the diastereomer may be accomplished by crystallization, chromatography, or any other method known in the art. For example, a preferred diastereomer has the configuration where C-6, C-7, C-9, C-13, and C-14 are respectively beta, beta, alpha, alpha, alpha, (see "6-beta, 7-beta" below). In another example, a preferred diastereomer has the configuration where C-6, C-7, C-9, C-13, and C-14 are respectively beta, alpha, alpha, alpha, alpha, alpha (see "6-beta, 7-alpha" below).

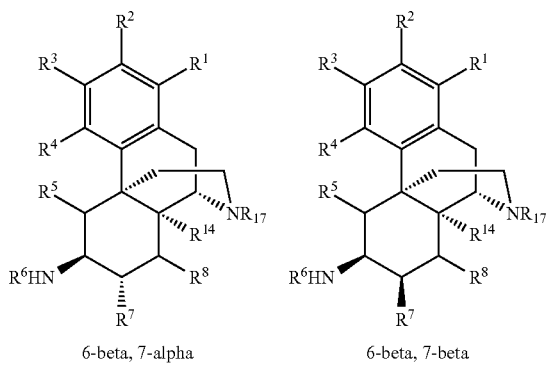

6-beta, 7-alpha      6-beta, 7-beta (III) Compositions (a) Formula (IV)

A further aspect of the invention encompasses a compound comprising Formula (IV) a compound comprising Formula (IV); and less than about 15% of a 6-alpha-amino epimer of the compound comprising Formula (IV):

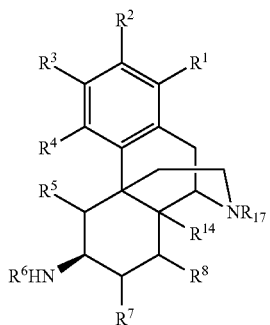

wherein:
$R^1$, $R^2$ and $R^5$ are hydrogen, hydrocarbyl, substituted hydrocarbyl, halogen, and $\{-\}OR^{15}$;
$R^3$ and $R^8$ are chosen from hydrogen, hydrocarbyl, substituted hydrocarbyl, and $\{-\}OR^{15}$;
$R^4$ is are chosen from hydrogen, hydrocarbyl, substituted hydrocarbyl, and $\{-\}OR^{15}$;
$R^6$ is chosen from hydrocarbyl and substituted hydrocarbyl;
$R^7$ is chosen from hydrocarbyl, substituted hydrocarbyl, and $\{-\}OR^{15}$;
$R^{14}$ is chosen from hydrogen and $\{-\}OR^{15}$;
$R^{15}$ is chosen from hydrogen, hydrocarbyl, substituted hydrocarbyl, a hydroxy protecting group; and
$R^{17}$ is chosen from hydrocarbyl, substituted hydrocarbyl, and protecting group.

In an exemplary embodiment, $R^1$, $R^2$, $R^5$ and $R^8$ are hydrogen; $R^2$ and $R^4$ are independently chosen from alkoxy hydroxy, and protected hydroxyl; $R^6$ is hydrocarbyl or substituted hydrocarbyl; $R^7$ is alkoxy or hydroxy; $R^{14}$ is hydrogen or hydroxyl; and $R^{17}$ is a hydrocarbyl chosen from alkyl, cycloalkyl, cycloalkylmethyl, alkynyl, aryl and heterocycle.

The composition may be epimerically or diastereomerically enriched. In certain embodiments, the 6-alpha-amino epimer is enriched such that the 6-alpha amino epimer comprises less than about 25%, or less than about 10%, or less than about 5%, or less than about 3%.

In further embodiments the compositions of Formula (IV) may comprise an enrichment of a single diastereomer. In one exemplary embodiment, the diastereomer is the 6-beta, 7-beta diastereomer shown above. In another exemplary embodiment, the diastereomer is the 6-beta, 7-alpha diastereomer above. In some embodiments, the 6-alpha-amino 7-alpha-$R^7$ diastereomer comprises less than about 10%, or less than about 5% or less than about 3%. In other embodiments, the 6-alpha-amino 7-beta-$R^7$ diastereomer comprises less than about 10%, or less than about 5% or less than about 3%.

(b) Formula (III)

In yet another aspect, the invention encompasses an intermediate compound comprising Formula (III); and less than about 15% of a 6-alpha-amino epimer of the compound comprising Formula (III):

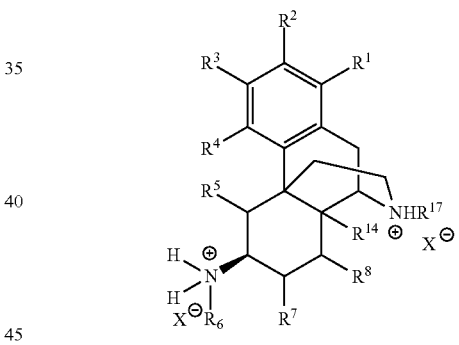

wherein:
$R^1$, $R^2$ and $R^5$ are hydrogen, hydrocarbyl, substituted hydrocarbyl, halogen, and $\{-\}OR^{15}$;
$R^3$ and $R^8$ are chosen from hydrogen, hydrocarbyl, substituted hydrocarbyl, and $\{-\}OR^{15}$;
$R^4$ is are chosen from hydrogen, hydrocarbyl, substituted hydrocarbyl, and $\{-\}OR^{15}$;
$R^6$ is chosen from hydrocarbyl and substituted hydrocarbyl;
$R^7$ is chosen from hydrocarbyl, substituted hydrocarbyl, and $\{-\}OR^{15}$;
$R^{14}$ is chosen from hydrogen and $\{-\}OR^{15}$;
$R^{15}$ is chosen from hydrogen, hydrocarbyl, substituted hydrocarbyl, a hydroxy protecting group;
$R^{17}$ is chosen from hydrocarbyl, substituted hydrocarbyl, and protecting group; and
X is an anion.

In an exemplary embodiment, $R^1$, $R^2$, $R^5$ and $R^8$ are hydrogen; $R^2$ and $R^4$ are independently chosen from alkoxy hydroxy, and protected hydroxyl; $R^6$ is hydrocarbyl or substituted hydrocarbyl; $R^7$ is alkoxy or hydroxy; $R^{14}$ is hydrogen or hydroxyl; and $R^{17}$ is a hydrocarbyl chosen from alkyl, cycloalkyl, cycloalkylmethyl, alkynyl, aryl and heterocycle.

The composition of intermediate compound (III) may be epimerically or diastereomerically enriched. In certain embodiments, the 6-alpha-amino epimer is enriched such that the 6-alpha amino epimer comprises less than about 25%, or less than about 10%, or less than about 5%, or less than about 3%.

In further embodiments the compositions of Formula (III) may comprise an enrichment of a single diastereomer. In one exemplary embodiment, the diastereomer is the 6-beta, 7-beta diastereomer shown above. In another exemplary embodiment, the diastereomer is the 6-beta, 7-alpha diastereomer above. In some embodiments, the 6-alpha-amino 7-alpha-$R^7$ diastereomer comprises less than about 10%, or less than about 5% or less than about 3%. In other embodiments, the 6-alpha-amino 7-beta-$R^7$ diastereomer comprises less than about 10%, or less than about 5% or less than about 3%.

Moreover, the compounds of the compositions (III) and (IV) may be pharmaceutically acceptable salts of the compound comprising Formulas (III) and (IV), as detailed above in section (II)(c).

The compositions of the invention may be formulated for administration by a number of different means that will deliver a therapeutically effective dose. Such formulations may be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980).

DEFINITIONS

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOK of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

As used herein, the term "6-amino" encompasses primary and secondary amine moieties conjugated to C-6 of a morphinan.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The term "enrichment" means an amount above the statistical distribution if all chiral centers had an equal probability of being alpha or beta.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting a particular moiety, wherein the protecting group may be removed, subsequent to the reaction for which the protection is employed, without disturbing the remainder of the molecule. Where the moiety is an oxygen atom (and hence, forming a protected hydroxy), exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxyethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Trac), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. When the moiety is an nitrogen atom (and hence, forming a protecting amine) exemplary protecting groups include benzyl, p-methoxyphenyl (PMP), 3,4-dimethoxybenxyl (PMB)), n-silyl groups, esters (e.g., benzoate (Bz), carbonyl (e.g. p-methoxybenzyl carbonyl (Moz), tert-butyloxycarbonyl (BOC), 9-fluorenylmethyloxycarbonyl (FMOC)), acetyl, carbamates, n-silyl groups and the like. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1

Preparation of 3,7-dimethoxy-17-methyl-6-(propylamino)morphian-4-ol 3,7-Dimethoxy-17-methyl-6-(propylamino)morphian-4-ol was prepared according to the following reaction scheme:

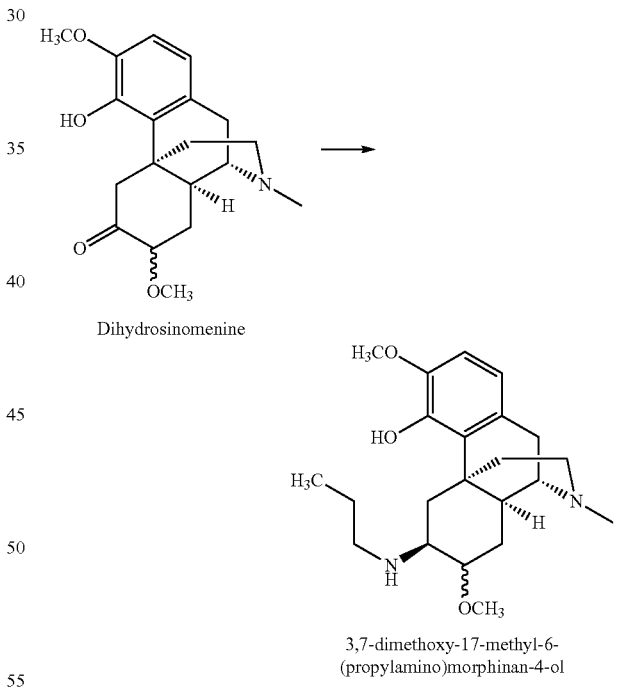

Dihydrosinomenine 3,7-dimethoxy-17-methyl-6-(propylamino)morphinan-4-ol

Dihydrosinomenine (0.005 mol) was mixed with n-propylamine (0.010 mol), triethylamine (0.010 mol) in 10 mL of acetonitrile. The reaction was cooled to 5° C. and formic acid (0.063 mol) was added dropwise to the solution. After warming to reaction temperature, dichloro(p-cymene)ruthenium (II) dimer (0.031 mmol) was added to the solution. The reaction was warmed to 60° C. and stirred for 48 hours, then cooled to room temperature and stirred for 24 hours. A precipitate formed, was filtered, rinsed, and dried. The solid was then slurried in distilled water (10 mL) and 29% $NH_3/H_2O$ was added dropwise to adjust the pH to 9.4. The solid was isolated by filtration, washed with distilled water, and dried under vacuum for 48 hours. The product was recovered as a singled diastereomer (0.004 mol). The filtrate was evaporated, extracted, and dried over anhydrous MgSO$_4$. The product was isolated by column chromatography by eluting with 1% CH$_3$OH/CHCl$_3$ to 4% CH$_3$OH/CHCl$_3$. The combined fractions were a mixture of diastereomers (0.0047 mol). Combined yield: 92%.

Example 2

Preparation of 3,7-dimethoxy-17-methyl-6-(isopropylamino)morphian-4-ol

Dihydrosinomenine (0.005 mol) was mixed with isopropylamine (0.010 mol), triethylamine (0.032 mol) in 11 mL of acetonitrile. The reaction was cooled to 5° C. and formic acid (0.060 mol) was added dropwise to the solution. After warming to reaction temperature, dichloro(p-cymene)ruthenium (II) dimer (0.0238 mmol) was added to the solution. The reaction was warmed to 60° C. and stirred for 48 hours, then cooled to room temperature and stirred for 24 hours. A precipitate formed, was filtered, rinsed, and dried. The solid was then slurried in distilled water (10 mL) and 29% NH$_3$/H$_2$O was added dropwise to adjust the pH to 9.4. The solid was isolated by filtration, washed with distilled water, and dried under vacuum for 48 hours. A product was recovered as a singled diastereomer (0.004 mol). The filtrate was evaporated, extracted, and dried over anhydrous MgSO$_4$. The product was isolated by column chromatography by eluting with 1% CH$_3$OH/CHCl$_3$ to 4% CH$_3$OH/CHCl$_3$. The combined fractions were a mixture of diastereomers (0.0041 mol). Combined yield: 87%.

Example 3

Preparation of 3,7-dimethoxy-17-methyl-6-(benzylamino)morphian-4-ol

Dihydrosinomenine (0.006 mol) was mixed with benzylamine (0.012 mol), triethylamine (0.029 mol) in 10 mL of acetonitrile. The reaction was cooled to 5° C. and formic acid (0.074 mol) was added dropwise to the solution. After warming to reaction temperature, dichloro(p-cymene)ruthenium (II) dimer (0.029 mmol) was added to the solution. The reaction was warmed to 60° C. and stirred for 36 hours, then cooled to room temperature and stirred for 24 hours. A precipitate formed, was filtered, rinsed, and dried. The solid was then slurried in distilled water (10 mL) and 29% NH$_3$/H$_2$O was added dropwise to adjust the pH to 9.2. The solution was then extracted with ethyl acetate, the extracts were combined and dried over anhydrous MgSO$_4$. The product was isolated as a mixture of diastereomers by column chromatography by eluting with 1% CH$_3$OH/CHCl$_3$ to 5% CH$_3$OH/CHCl$_3$. Combined yield: 87%.

Example 4

Preparation of 3,7-dimethoxy-17-methyl-6-(methylamino)morphian-4-ol

Dihydrosinomenine (0.005 mol) was mixed with isopropylamine (0.010 mol), triethylamine (0.032 mol) in 11 mL of acetonitrile. The reaction was cooled to 5° C. and formic acid (0.060 mop was added dropwise to the solution. After warming to reaction temperature, dichloro(p-cymene)ruthenium (II) dimer (0.0238 mmol) was added to the solution. The reaction was warmed to 60° C. and stirred for 48 hours, then cooled to room temperature and stirred for 24 hours. A precipitate formed, was filtered, rinsed, and dried. The solid was then slurried in distilled water (10 mL) and 29% NH$_3$/H$_2$O was added dropwise to adjust the pH to 9.4. The solid was isolated by filtration, washed with distilled water, and dried under vacuum for 48 hours. A product was recovered as a singled diastereomer (0.004 mol). The filtrate was evaporated, extracted, and dried over anhydrous MgSO4. The product was isolated by column chromatography by eluting with 1% CH$_3$OH/CHCl$_3$ to 4% CH$_3$OH/CHCl$_3$. The combined fractions were a mixture of diastereomers (0.0041 mol). Combined yield: 87%.

Example 5

Preparation of 3,7-dimethoxy-17-methyl-6-(benzylamino)morphian-4-ol

Dihydrosinomenine (0.004 mol) was mixed with methylamine HCl (0.009 mol), triethylamine (0.021 mol) in 10 mL of acetonitrile. The reaction was cooled to 5° C. and formic acid (0.074 mol) was added dropwise to the solution. After warming to reaction temperature, dichloro(p-cymene)ruthenium (II) dimer (0.029 mmol) was added to the solution. The reaction was warmed to 60° C. and stirred for 48 hours, then cooled to room temperature and stirred for 24 hours. A precipitate formed, was filtered, rinsed, and dried. The solid was then slurried in distilled water (10 mL) and 29% NH$_3$/H$_2$O was added dropwise to adjust the pH to 9.2. The solution was then extracted with ethyl acetate, the extracts were combined and dried over anhydrous MgSO$_4$. The product was isolated as a mixture of diastereomers by column chromatography by eluting with 1% CH$_3$OH/CHCl$_3$ to 5% CH$_3$OH/CHCl$_3$. Combined yield: 87%.

Example 6

Preparation of 3,7-dimethoxy-17-methyl-6-(ethanolamino)morphian-4-ol

Dihydrosinomenine (0.005 mol) was mixed with ethanolamine (0.010 mol), triethylamine (0.025 mol) in 10 mL of acetonitrile. The reaction was cooled to 5° C. and formic acid (0.062 mol) was added dropwise to the solution. After warming to reaction temperature, dichloro(p-cymene)ruthenium (II) dimer (0.0249 mmol) was added to the solution. The reaction was warmed to 60° C. and stirred for 48 hours, then cooled to room temperature and stirred for 24 hours. A precipitate formed, was filtered, rinsed, and dried. The solid was then slurried in distilled water (10 mL) and 29% NH$_3$/H$_2$O was added dropwise to adjust the pH to 9.4. The solution was then extracted with ethyl acetate, the extracts were combined and dried over anhydrous MgSO$_4$. The product was isolated as a mixture of diastereomers by column chromatography by eluting with 1% CH$_3$OH/CHCl$_3$ to 4% CH$_3$OH/CHCl$_3$. Combined yield: 80%.

Example 7

Preparation of 3,7-dimethoxy-17-methyl-6-(β-alanine methyl ester)morphian-4-ol

Dihydrosinomenine (0.005 mol) was mixed with β-alanine methyl ester HCl (0.010 mol), triethylamine (0.024 mol) in 10 mL of acetonitrile. The reaction was cooled to 5° C. and formic acid (0.060 mol) was added dropwise to the solution.

After warming to reaction temperature, dichloro(p-cymene) ruthenium (II) dimer (0.0249 mmol) was added to the solution. The reaction was warmed to 60° C. and stirred for 48 hours, then cooled to room temperature and stirred for 24 hours. A precipitate formed and was removed by filtration. The filtrate was then evaporated to an oil, and 20 mL of distilled water was added and the pH was adjusted to 9.6 by adding 29% $NH_3/H_2O$ dropwise to the solution. The solution was then extracted with ethyl acetate, the extracts were combined and dried over anhydrous $MgSO_4$, and evaporated to dryness. The product was isolated as a mixture of diastereomers. Combined yield: 87%.

Example 8

Preparation of 3,7-dimethoxy-17-methyl-6-(glycine ethyl ester)morphian-4-ol

Dihydrosinomenine (0.005 mol) was mixed with glycine ethyl ester HCl (0.007 mol), triethylamine (0.024 mol) in 15 mL of acetonitrile. The reaction was cooled to 5° C. and formic acid (0.047 mol) was added dropwise to the solution. After warming to reaction temperature, dichloro(p-cymene) ruthenium (II) dimer (0.0249 mmol) was added to the solution. The reaction was warmed to 60° C. and stirred for 48 hours, then cooled to room temperature and stirred for 24 hours. The mixture was then evaporated to an oil and 20 mL of acetonitrile and stirred for 24 hours. The oil was then evaporated and 20 mL of distilled water was added and the pH was adjusted to 9.4 by adding 29% $NH_3/H_2O$ dropwise to the solution. The solution was then extracted with ethyl acetate, the extracts were combined and dried over anhydrous $MgSO_4$, and evaporated to dryness. The product was isolated as a mixture of diastereomers. Combined yield: 89%.

Example 9

Preparation of 3,7-dimethoxy-17-methyl-6-(alanine)morphian-4-ol

Dihydrosinomenine (0.005 mol) was mixed with alanine (0.010 mol), triethylamine (0.025 mol) in 15 mL of acetonitrile. The reaction was cooled to 5° C. and formic acid (0.061 mol) was added dropwise to the solution. After warming to reaction temperature, dichloro(p-cymene)ruthenium (II) dimer (0.0249 mmol) was added to the solution. The reaction was warmed to 60° C. and stirred for 48 hours, then cooled to room temperature and stirred for 24 hours. The mixture was then evaporated to an oil. 20 mL of distilled water was added and the pH was adjusted to 9.4 by adding 29% $NH_3/H_2O$ dropwise to the solution. The solution was then extracted with ethyl acetate, the extracts were combined and dried over anhydrous $MgSO_4$, and evaporated to dryness. The product was isolated as a mixture of diastereomers by column chromatography with a gradient from 1% $CH_3OH/CHCl_3$ to 4% $CH_3OH/CHCl_3$. Combined yield: 62%.

What is claimed is:

1. A process for preparing a 6-amino morphinan, the process comprising mixing dihydrosinomenine with an amine source comprising the formula $R^6NH_2$, wherein $R^6$ is selected from the group consisting of hydrogen, hydrocarbyl, and substituted hydrocarbyl, a hydrogen donor comprising a formate ion, a transition metal catalyst, and a proton acceptor, wherein the proton acceptor is chosen from ammonia, ammonium hydroxide, and sodium hydroxide; to produce the 6-amino morphinan, wherein at least one intermediate compound comprising a 6-imine moiety is produced during the process; and wherein the process avoids the use of hydrogen gas, and wherein the 6-amino morphinan product comprises an amount of the 6-alpha epimer less than 10%.

* * * * *